(12) United States Patent
Rezach et al.

(10) Patent No.: US 8,317,834 B2
(45) Date of Patent: Nov. 27, 2012

(54) PRE-ASSEMBLED CONSTRUCT FOR INSERTION INTO A PATIENT

(75) Inventors: William A Rezach, Atoka, TN (US);
Douglas N Baker, Collierville, TN (US);
Allison Gasperut, Boulder, CO (US);
Douglas D Kave, Byhalia, MS (US);
Anthony Harrison, Atoka, TN (US);
Christopher Nelson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 301 days.

(21) Appl. No.: 12/695,384

(22) Filed: Jan. 28, 2010

(65) Prior Publication Data

US 2011/0184416 A1    Jul. 28, 2011

(51) Int. Cl.
*A61B 17/70* (2006.01)
(52) U.S. Cl. ......... 606/264; 606/259; 606/261; 606/275
(58) Field of Classification Search .................. 606/246, 606/259, 261, 264–278, 316; 411/190–336
See application file for complete search history.

(56) References Cited

U.S. PATENT DOCUMENTS

| | | |
|---|---|---|
| 5,102,412 A | 4/1992 | Rogozinski |
| 5,545,167 A | 8/1996 | Lin |
| 5,584,833 A | 12/1996 | Fournet-Fayard et al. |
| 5,921,985 A | 7/1999 | Ross, Jr. et al. |
| 6,231,575 B1 | 5/2001 | Krag |
| 7,104,992 B2 | 9/2006 | Bailey |
| 7,306,602 B2 | 12/2007 | Bono et al. |
| 7,344,537 B1 | 3/2008 | Mueller |
| 7,578,833 B2 | 8/2009 | Bray |
| 2001/0029374 A1 | 10/2001 | Kikuchi et al. |
| 2004/0158251 A1 | 8/2004 | Morrison et al. |
| 2004/0215190 A1 | 10/2004 | Nguyen et al. |
| 2004/0215191 A1 | 10/2004 | Kitchen |
| 2004/0236328 A1 | 11/2004 | Paul et al. |
| 2004/0243146 A1 | 12/2004 | Chesbrough et al. |
| 2006/0111712 A1 | 5/2006 | Jackson |
| 2009/0264931 A1 | 10/2009 | Miller et al. |

*Primary Examiner* — Ellen C Hammond (57) ABSTRACT

Surgical constructs pre-assembled for insertion as a unit into a patient. The pre-assembled construct may include an elongated member with opposing first and second ends. The construct may also include a connector with a body, a first receptacle that extends through the body and receives the elongated member, a threaded aperture that extends from an exterior of the body into the first receptacle, a fastener threaded into the threaded aperture, and a second receptacle that receives a structural member in the patient. The first receptacle may be larger than the elongated member for the connector to be movable along the elongated member. The construct may also include retaining members permanently attached to each of the first and second ends of the elongated member. The retaining members may include a central opening with an inner radial surface that contacts the elongated member and an outer radial surface that extends outward beyond the elongated member. The retaining members may be larger than the first receptacle to prevent the connector from detaching from the elongated member.

9 Claims, 8 Drawing Sheets

PRE-ASSEMBLED CONSTRUCT FOR INSERTION INTO A PATIENT

BACKGROUND

The present application is directed to a construct that is pre-assembled prior to being implanted into a patient to facilitate the insertion process, handling by the surgeon, and prevent detachment of one or more of the components.

Various different constructs are implanted into patients during surgical procedures. The constructs may connect to one or more elongated members, bone anchors, and various implant devices. The constructs often include multiple separate components that are attached together. Often times the components are physically small which makes them difficult to handle during the surgical procedure. The physical size may also make the components difficult to attach together during the surgical procedure. Further, the working area for the surgeon to implant the constructs is often relatively small. The small size may be the result of the patient anatomy and/or the type of construct being implanted into the patient. The working area may be further constrained by other surgical instruments that are within the patient at various times during the surgical procedure.

Some existing constructs include separate components that are attached together by the surgeon during the surgical process. This is often difficult for the surgeon because of the small size of the components and the relatively small working area.

SUMMARY

The present application is directed to constructs that are pre-assembled prior to being implanted into a patient and methods of assembling the construct prior to implantation. The pre-assembled construct may include an elongated member with opposing first and second ends. The construct may also include a connector that includes a body, a first receptacle that extends through the body and receives the elongated member with the first end positioned on a first side of the connector and the second end positioned on a second side of the connector, a threaded aperture that extends from an exterior of the body into the first receptacle, a fastener threaded into the threaded aperture, and a second receptacle that receives a structural member. The first receptacle may be larger than the elongated member for the connector to be movable along the elongated member. The construct may also include retaining rings permanently attached to each of the first and second ends of the elongated member. The retaining rings may include a central opening with an inner radial surface that contacts the elongated member and an outer radial surface that extends outward beyond the elongated member. The retaining rings may be larger than the first receptacle to prevent the connector from detaching from the elongated member.

The construct may also include the fastener attached to the connector to prevent inadvertent detachment. The fastener may include a thread that extends along first and second longitudinal sections and an interrupt in a valley of the thread positioned between the sections. The interrupt may prevent or resist the first section from moving into the threaded aperture. The fastener may also be configured with the interrupt and the first section positioned in the first receptacle for a distal end of the fastener to contact against the elongated member.

The application also includes methods of assembling a construct prior to insertion into a patient. A method may include assembling together a connector from a plurality of components with the connector including a receptacle and a fastener that extends into the receptacle. The method may include attaching a first retaining member to a first end of the elongated member and a second retaining member to a second end of the elongated member. The first retaining member may be constructed from a flexible material and have a first orientation that is larger than the receptacle and the second retaining member may be larger than the receptacle. The method may also include inserting the first end of the elongated member into the receptacle and temporarily deforming the first retaining member from the first orientation to a second orientation that is smaller than the receptacle. The method may include moving the connector over and past the first retaining member and towards the central section and causing the first retaining member to return to the first orientation. The method may include tightening the fastener and fixedly positioning the connector relative to the elongated member. Once the construct is assembled, it may be implanted into the patient.

The various aspects of the various embodiments may be used alone or in any combination, as is desired.

DETAILED DESCRIPTION

Figure 1:
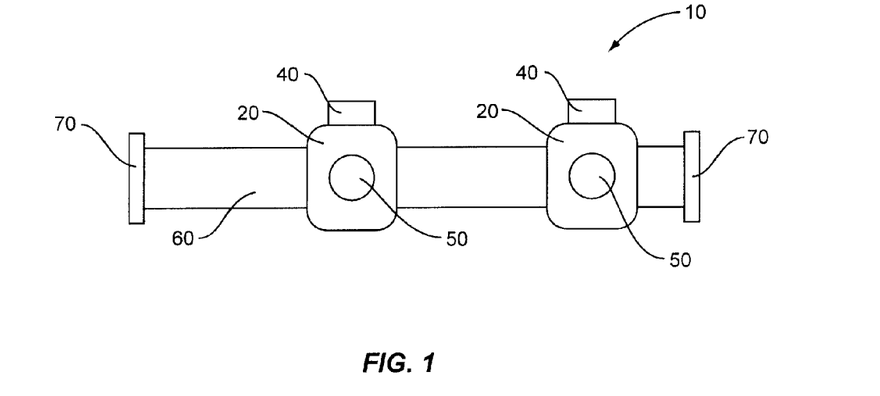
FIG. 1 is a schematic diagram of a construct according to one embodiment.

The present application is directed to a construct with a number of separate components that are pre-assembled prior to insertion into a patient. The pre-assembled construct 10 can be inserted and positioned within a patient without detachment of the separate components. FIG. 1 illustrates a construct 10 with a pair of connectors 20 attached to an elongated member 60. A fastener 40 may be attached to each of the connectors 20 in a manner to prevent detachment. The fastener 40 may be tightened to contact against the elongated member 60 and fix the relative position of each connector 20. One or more retaining members 70 may maintain the connectors 20 attached to the elongated member 60. The connectors 20 may also include a receptacle 50 to attach with an additional element. The pre-assembled condition prevents the components from detaching from the construct 10 and facilitates handling of the construct 10 by a surgeon.

Figure 2:
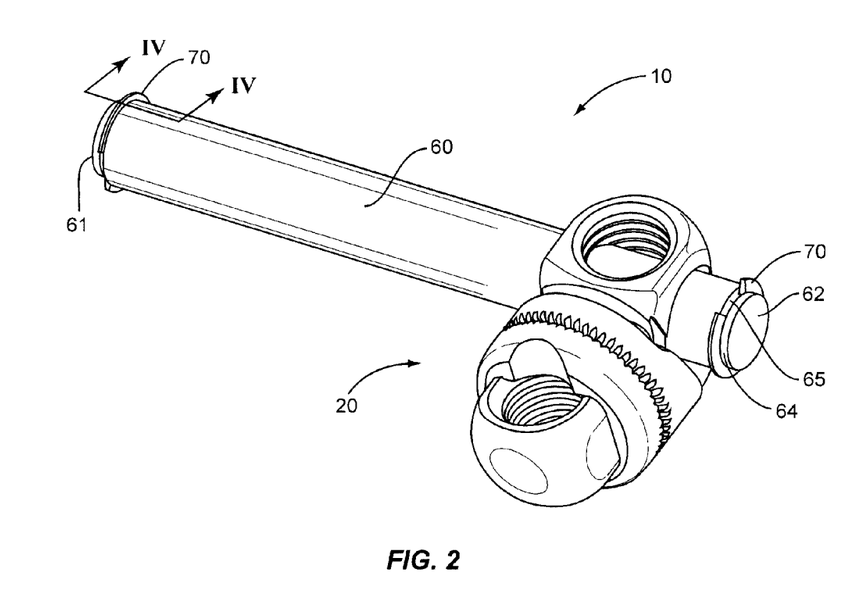
FIG. 2 is a perspective view of a pre-assembled construct according to one embodiment.

FIG. 1 includes the pre-assembled construct 10 with a pair of connectors 20. Constructs 10 may include various numbers of connectors 20, including a single connector 20 as illustrated in FIG. 2. Constructs 10 may also include three or more connectors 20.

Figure 3:
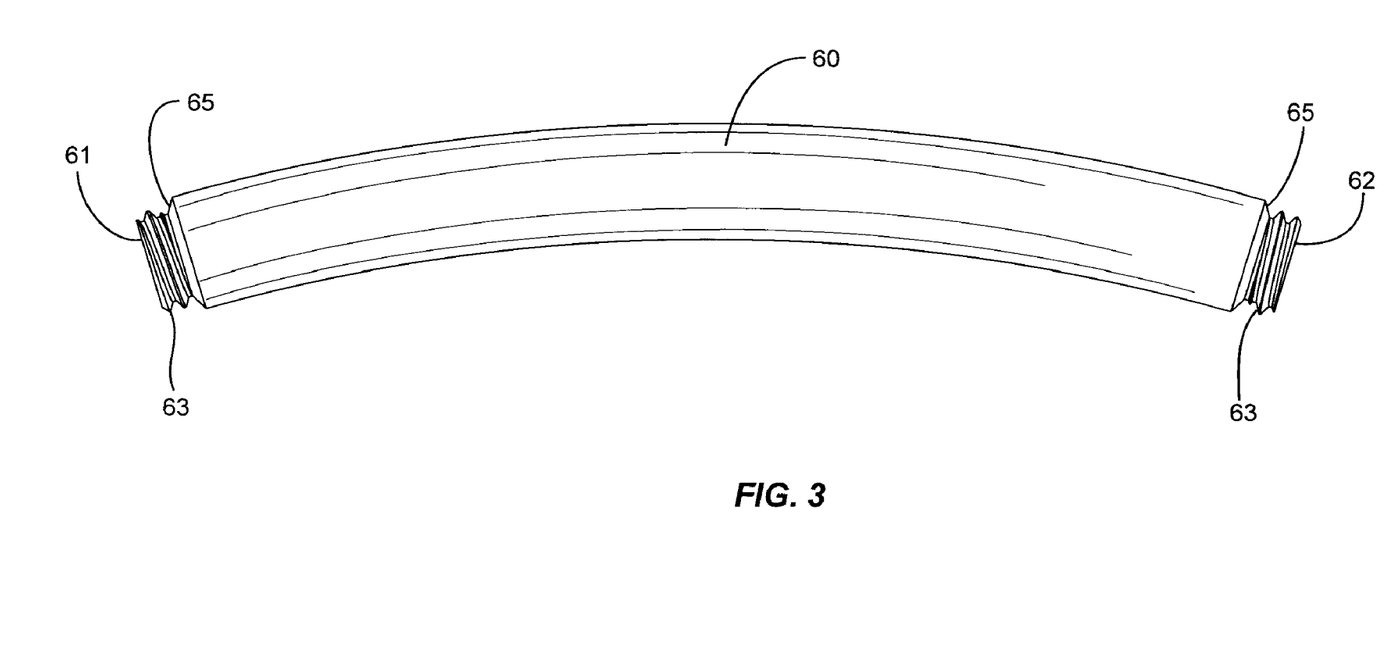
FIG. 3 is a side view of an elongated member according to one embodiment.

The elongated member 60 includes an elongated shape with a first end 61 and a second end 62. The elongated member 60 may be a rod constructed from various materials, including but not limited to stainless steel, titanium, PEEK, and ceramic. The elongated member 60 may be substantially straight as illustrated in FIG. 2, or may be curved as illustrated in FIG. 3. The elongated member 60 may be curved along the entire length (i.e., from the first end 61 to the second end 62 as illustrated in FIG. 3), or may include a discrete curved section. The elongated member 60 may include various cross-sectional shapes including but not limited to circular, oval, and polygonal.

Figure 4:
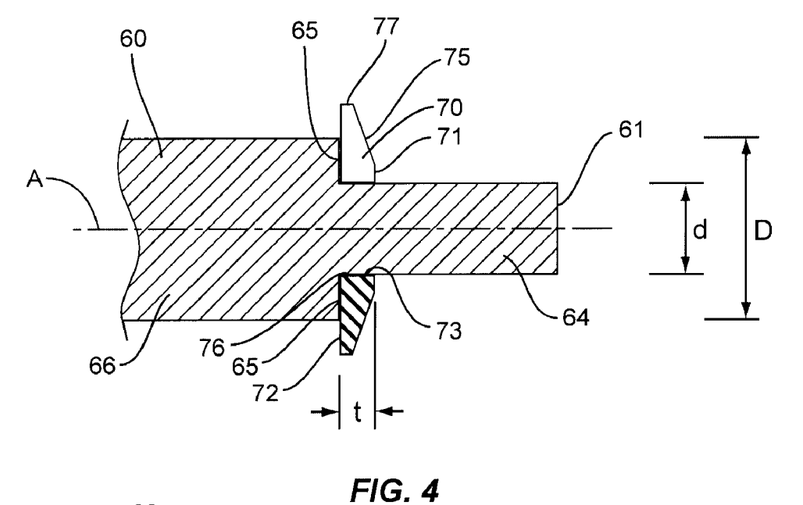
FIG. 4 is a sectional view taken along line IV-IV of FIG. 2.
Figure 5:
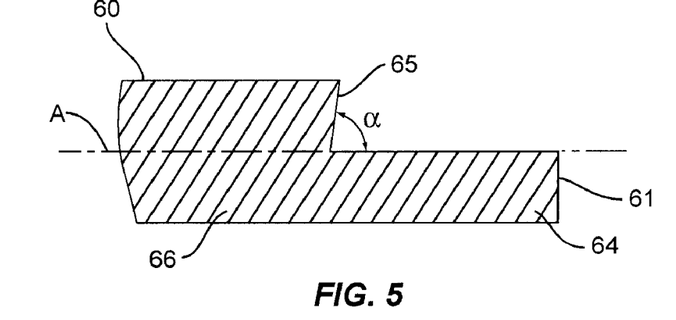
FIG. 5 is a section view of a portion of an elongated member according to one embodiment.

The elongated member 60 includes connection features at one or both ends 61, 62 to receive the retaining members 70. FIG. 4 includes a retaining feature that consists of a longitudinal section with a reduced size 64. The reduced section 64 extends inward a discrete distance from the end 61. This reduced section 64 includes a smaller size d than a size D of a central section 66 of the elongated member 60. In the embodiment of FIG. 4, the sections 64, 66 each include circular cross-sectional shapes and the sizes d, D are diameters. FIG. 4 includes each of the sections 64, 66 having uniform dimensions and being centered along the longitudinal axis A. This positioning results in the central section 66 extending radially outward in every direction beyond the reduced section 64. In other embodiments, one or both sections 64, 66 may include various shapes and dimensions and the sizes may vary. The central section 66 may include a larger size in only a limited direction. FIG. 5 includes the reduced section 64 being offset from the longitudinal axis A of the elongated member 60. The central section 66 extends radially outward beyond the reduced section 64 in only a limited direction.

The reduced section 64 extends inward from the end 61 and terminates at a wall 65. FIG. 4 includes the wall 65 substantially perpendicular to a longitudinal axis A of the elongated member 60. Other embodiments may include the wall 65 oriented at a non-perpendicular angle, such as FIG. 5 with the wall 65 oriented at an acute angle α relative to the longitudinal axis A.

Another connection feature includes threads 63 positioned at one or both ends 61, 62 of the elongated member 60 as illustrated in FIG. 3. The threads 63 extend inward a discrete distance from the ends 61, 62.

The elongated member 60 may include a connection feature on one or both ends 61, 62. In embodiments with two connection features, the features may be the same on each end 61, 62, or include different features on each end.

The retaining members 70 attach to the ends 61, 62 to maintain the connector 20 attached to the elongated member 60. In a preferred embodiment, the construct 10 includes a retaining member 70 at each end 61, 62 of the elongated member 60. Other embodiments may include a single retaining member 70 at just one of the ends 61, 62. The retaining members 70 may be constructed from a variety of materials, including but not limited to Nitinol, and various non-metallic materials including but not limited to silicone elastomers.

Figure 6:
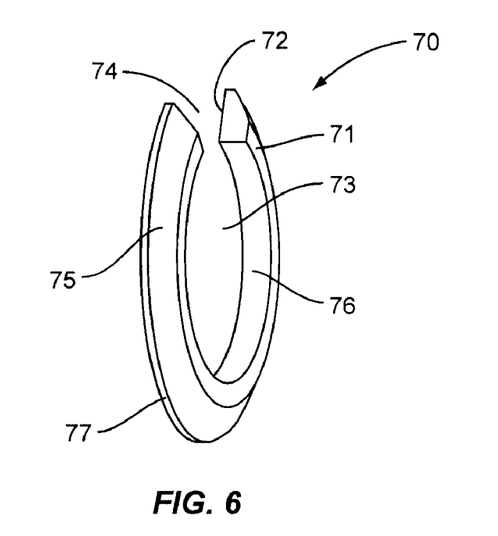
FIG. 6 is a perspective view of a retaining member according to one embodiment.

FIG. 6 includes a retaining member 70 with an outer axial surface 71 that faces away from the central section 66 of the elongated member 60 and an opposing inner axial surface 72. One of both surfaces 71, 72 may be configured to give the retaining member 70 a variable width to facilitate attachment of the connector 20 as will be explained in more detail below. FIG. 6 includes the outer surface 71 with a chamfer 75 and the inner surface 72 being substantially flat to abut against the wall 65 (see FIG. 4). The retaining member 70 further includes an inner radial surface 76 and an outer radial surface 77. The retaining member 70 has a substantially C-shape with a central opening 73 and gap 74. The retaining member 70 may also include a shape that completely extends around the central opening 73 (e.g., O-shape).

FIG. 4 illustrates the retaining member 70 attached to the elongated member 60. The retaining member 70 is seated with the inner radial surface 76 abutting against the reduced section 64. The outer radial surface 77 is positioned radially outward beyond the central section 66 of the elongated member 60. Further, the inner axial surface 72 abuts against the wall 65. The chamfer 75 faces axially outward away from the central section 66. The chamfer 75 gives the retaining member 70 a variable thickness t. FIG. 4 includes the chamfer 75 beginning at a point that is radial outward away from the inner surface 76. Therefore, the thickness t is constant for a first inward radial section, and decreases along a second outward radial section. FIG. 4 includes the first section positioned radially inward from the outer surface of the central section 66. This positioning provides for the retaining member 70 to deform inward towards the central section 66 when the connector 20 is loaded onto the elongated member 60 and moved over the retaining member 70. In other embodiments, the width of the retaining member 70 measured between the outer and inner surfaces 71, 72 may be substantially constant.

Figure 7:
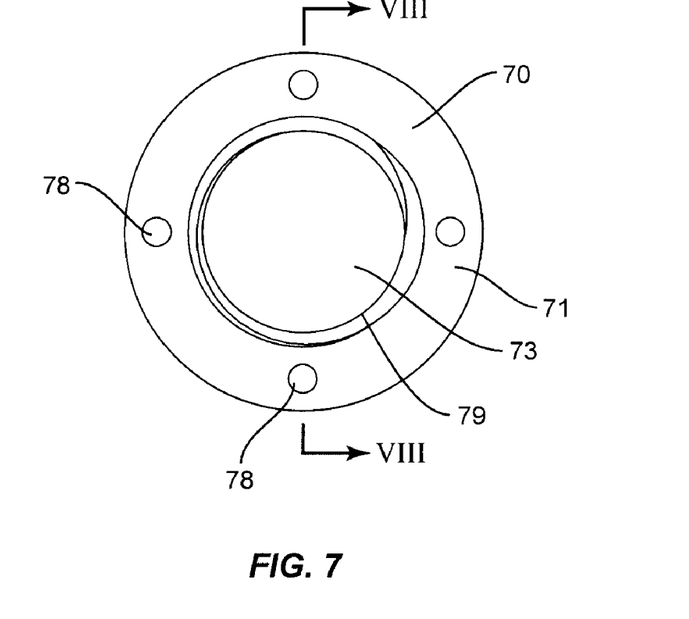
FIG. 7 is a side view of a retaining member according to one embodiment.
Figure 8:
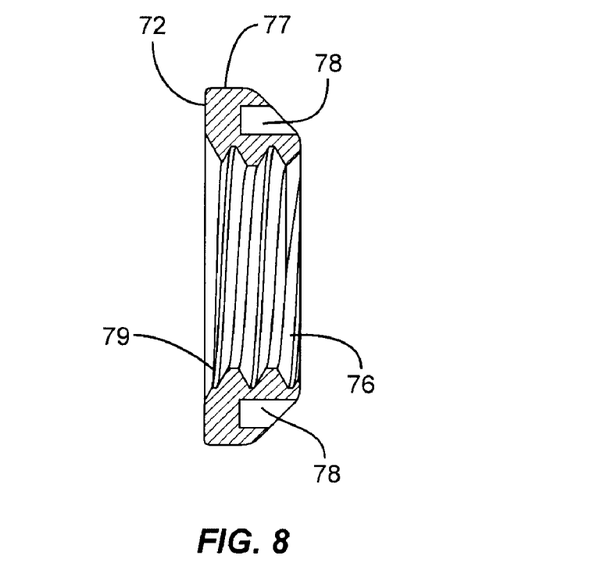
FIG. 8 is a sectional view taken along line VIII-VIII of FIG. 7.

The retaining members 70 may be attached to the elongated member 60 in various different manners. In one embodiment, the retaining member 70 is flexible and can be enlarged and snapped onto the elongated member 60. The retaining member 70 may also be threaded onto the elongated member 60. FIGS. 7 and 8 illustrate the inner radial surface 76 including threads 79 that engage with threads 63 on the elongated member 60. The retaining member 70 may be attached in various other manners, including but not limited to adhesives, mechanical fasteners, and laser welding. In one specific embodiment, the threads 63 and the elongated member 60 and/or threads 79 on the retaining member 70 are laser welded at discrete locations to attach the retaining member 70. Further, the retaining members 70 may be attached using multiple attachments (e.g., threads and adhesives) to further ensure attachment to the elongated member 60. After attachment, a torque may be applied to the retaining members 70 to ensure they are adequately attached to the elongated member 60.

As illustrated in FIGS. 7 and 8, one or more cavities 78 may extend into the retaining member 70. The cavities 78 may be spaced apart around the retaining member 70, and may extend a limited distance into the outer surface 71. The cavities 78 provide points for applying a torque to the retaining member 70 to adequately thread the member onto the elongated member 60. The cavities 78 may also be used to verify that the retaining member 70 is adequately attached to the elongated member 60.

The connector 20 is attached to the elongated member 60 and maintained by the retaining members 70. The connector 20 attaches the construct 10 to another structural element. The connector 20 may connect to a bone anchor for attaching the construct 10 to bony anatomy within the patient. The connector 20 may also connect to another elongated member.

Figure 9:
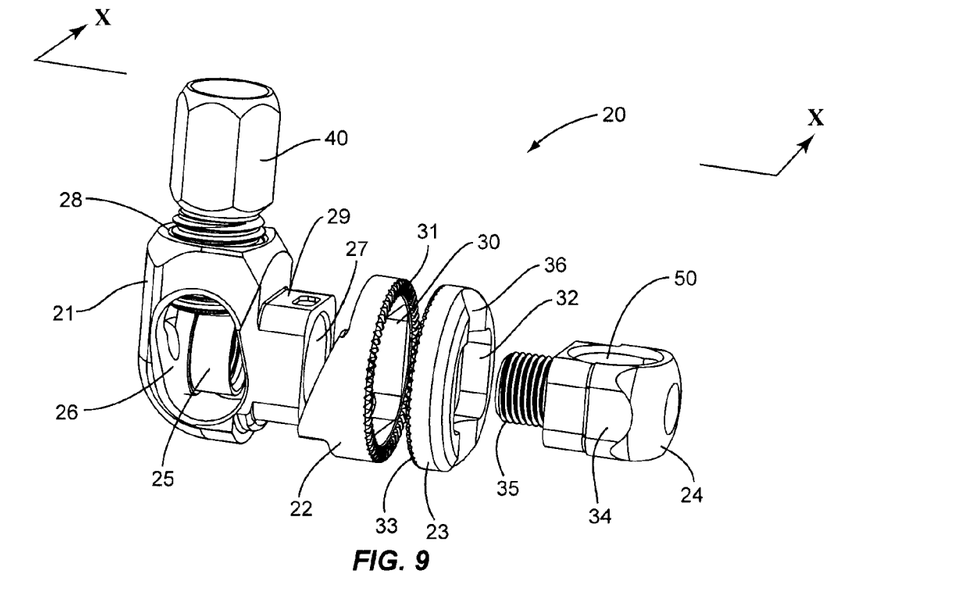
FIG. 9 is an exploded perspective view of a connector according to one embodiment.
Figure 10:
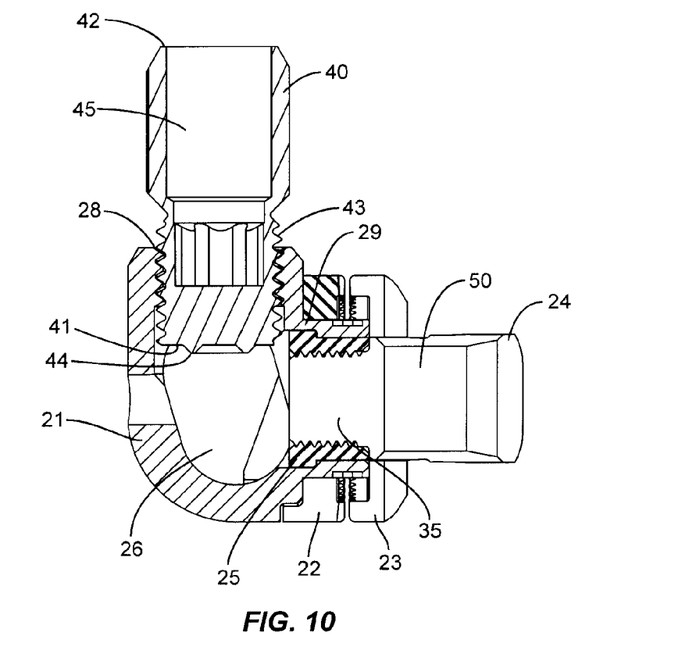
FIG. 10 is a sectional view taken along line X-X of FIG. 9 and illustrates an assembled connector prior to placement on an elongated member.

Various types of connectors 20 may be included as part of the construct 10. FIG. 9 includes an exploded view of a connector 20 that includes a first receptacle 26 to receive the elongated member 60 and a second receptacle 50 to receive an additional element. The connector 20 also includes a body 21 that includes the first receptacle 26, a fastener 40 that extends into the receptacle 26, a nut 25, a pair of washers 22, 23, and a receiver 24 that includes the second receptacle 50.

The body 21 includes the first receptacle 26 that receives the elongated member 60, and first and second openings 27, 28 that extend into the first receptacle 26. The first opening 27 extends into the first receptacle 26 from a first direction. The first opening 27 is formed within a neck 29 that extends outward from the body 21 away from the first receptacle 26. The second opening 28 extends into the first receptacle 26 from an opposing direction and is threaded to receive the fastener 40.

The fastener 40 fits within the second opening 28 in the body 21 and extends into the first receptacle 26 to contact against the elongated member 60. The fastener 40 includes a distal end 41 and a proximal end 42 and is threaded to engage with corresponding threads in the opening 28. The distal end 41 may include one or more protrusions 44 with sharpened tips that contact against elongated member 60. The proximal end 42 may include a polygonal sectional shape to engage with an engagement tool for rotating the fastener 40 relative to the body 21. A cavity 45 may extend into the proximal end 42.

The fastener 40 is movable relative to the body 21 to adjust the size of the first receptacle 26. The first receptacle 26 is larger than the elongated member 60 for the connector 20 to move along the longitudinal length of the elongated member 60. Once positioned, the fastener 40 is tightened to contact against and fix the longitudinal position of the connector 20.

Figure 11:
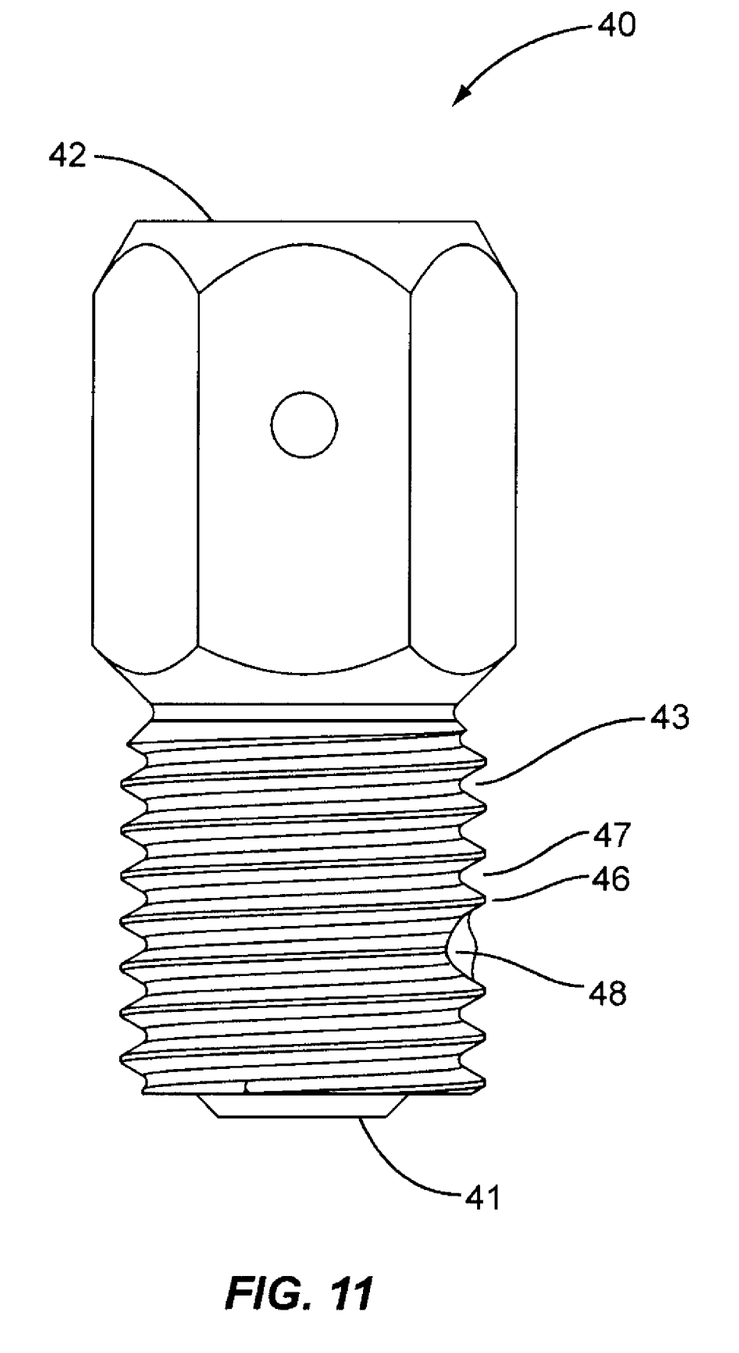
FIG. 11 is a side view of a fastener with a thread and an interrupt according to one embodiment.

The fastener 40 includes a thread 43 as illustrated in FIG. 11. The thread 43 extends between a first point at or in proximity to the distal end 41 and a second point in closer proximity to the proximal end 42. The thread 43 includes a crest 46 and a root 47. An interrupt 48 is positioned along the thread 43 between the first and second points. The interrupt 48 is a break in the thread 43 that prevents engagement with the threaded opening 28 and maintains attachment of the fastener 40 with the body 21. The interrupt 48 and the distal section of the fastener 40 are positioned outward beyond the opening 28. In one embodiment, this positions the interrupt 48 and distal section within the first receptacle 26.

The interrupt 48 may be formed in the thread 43 after the fastener 40 is threaded into the opening 28. The fastener 40 is threaded into the opening 28 an amount for a distal section to extend outward beyond the opening 28 and into the first receptacle 26. The interrupt 48 is then formed by deforming the thread 43 at the desired location. In one embodiment, the thread 43 is exposed in the first receptacle 26 and a laser is directed into the first receptacle 26. The laser melts the crest 46 of the thread 46 and deforms it into the adjacent root 47. This deformation forms a solid interrupt 48 without creating burrs that could break off into the patient. The interrupt 48 may extend over a single rotation or multiple rotations of the thread 43. The interrupt 48 may also be formed by contacting the thread 46 with a deformation tool. A force is applied to the thread 46 through the tool thus creating the interrupt 48. The interrupt 48 may also be formed with an adhesive, such as a silicone adhesive, that is applied to the thread 46. The interrupt 48 formed by the adhesive may or may not further include the thread 46 being physically deformed.

The connector 20 also includes washers 22, 23 that each attach to the body 21 and are configured to adjust the angle of the receiver 24. The washers 22, 23 each include an opening 30, 32 respectively that align with the opening 27 in the body 21. The opening 30 in the first washer 22 may include a shape that matches the sectional shape of the neck 29. These corresponding shapes allow the first washer 22 to seat onto the neck 29 and prevent relative rotation. The opening 32 of the second washer 23 may correspond to the sectional shape of the receiver 24 as will be explained below. The splines 31, 33 are positioned on opposing faces and mate together at the desired angular position when the connector 20 is assembled together. The second washer 23 may also include a scalloped section 36 that faces outward towards the receiver 24. The scalloped section 36 conforms to the exterior shape of the structural member received in the second receptacle 50.

The receiver 24 includes the second receptacle 50 to receive the additional structural element, such as another elongated member or a bone anchor. The receiver 24 includes a main section 34 that forms the receptacle 50 and an extension 35. The receptacle 50 may include an elongated shape with a major axis that aligns with the openings 27, 30, 32, and a perpendicular minor axis. The extension 35 may be threaded and extend outward from the main section 34 and is received within the threaded nut 25. The sectional shape of the main section 34 may correspond to the sectional shape of the opening 32 for the main section 34 to seat within the opening 32 when the threaded extension 35 mates with the nut 25.

One example of a connector is disclosed in U.S. Pat. No. 7,261,715 herein incorporated by reference in its entirety. Other connectors include spinal systems TSRH 3D and TSRH 3Dx spinal available from Medtronic Inc., Spinal and Biologics, of Memphis, Tenn.

In use, the construct 10 is pre-assembled prior to insertion into the patient. The assembly may be completed at an off-site location (e.g., at the manufacturer) or at the time of the surgical procedure and prior to insertion. A benefit of the assembly at the time of the procedure is the ability to specifically tailor the construct to the specific needs of the patient. This may also reduce inventory of components as it may not be necessary to stock a variety of fully assembled constructs. Some embodiments of the construct 10 may not include the fastener 40 having an interrupt 48 along the thread 43. In embodiments with the interrupt 48, the interrupt 48 is usually completed off-site such as at the manufacturer.

Figure 12:
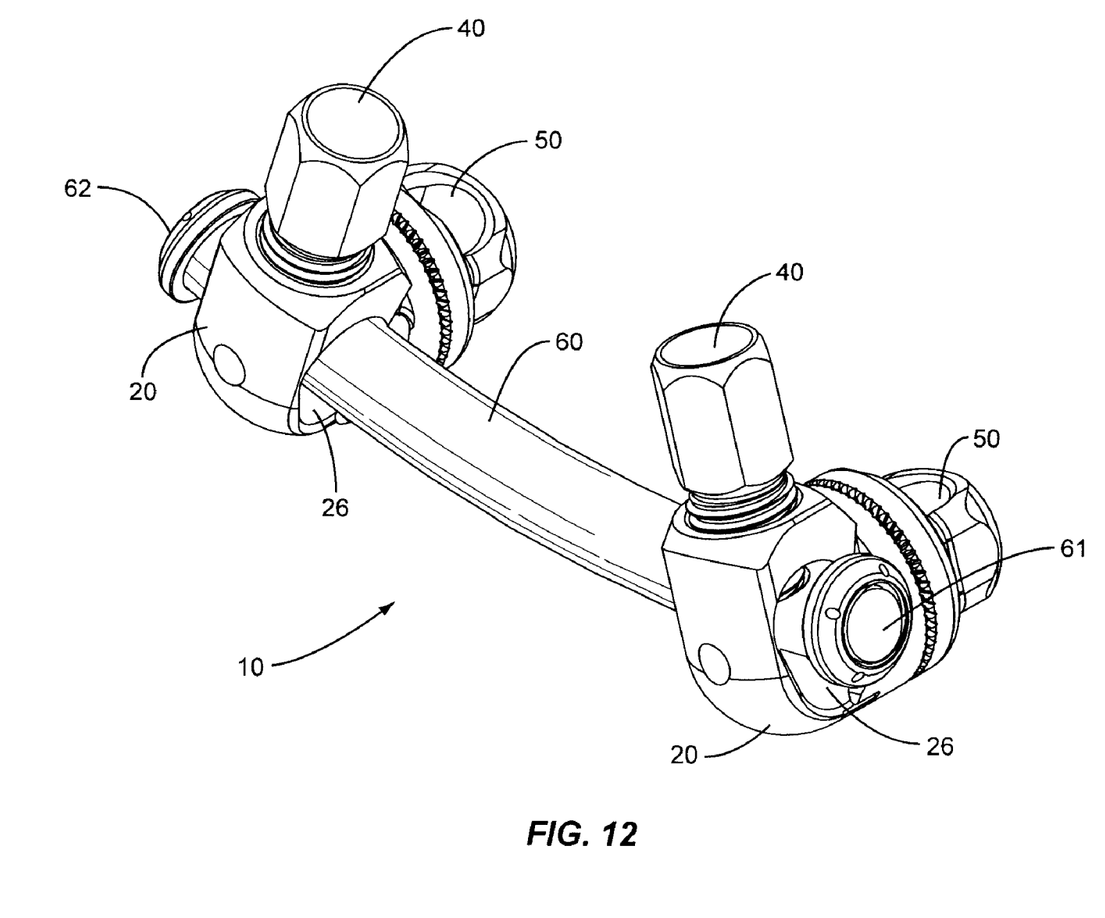
FIG. 12 is a perspective view of a pre-assembled construct according to one embodiment.

The assembly process may include the connector 20 being assembled together with the desired components. Once assembled, the connector 20 may be attached to the elongated member 60. This may include an end 61, 62 of the elongated member 60 being inserted into the first receptacle 26 and the connector 20 moved along the elongated member 60 to a central section 66. Once positioned, retaining members 70 may be attached to one or both ends 61, 62. The retaining members 70 are larger than the first receptacle 26 and prevent the connector 20 from detaching from the elongated member 60. FIG. 12 illustrates a pre-assembled construct 10 that is ready for insertion into the patient.

In one embodiment, the pre-assembled construct 10 is configured to connect to vertebral members. The elongated member 60 is a vertebral rod that has a length to extend along the desired vertebral levels. Prior to insertion of the construct 10, at least two bone anchors are attached to the vertebral members. Further, anchor posts are attached to each of the bone anchors and extend outward away from the vertebral members. The pre-assembled construct 10 includes a pair of connectors 20 each with a second receptacle 50 as illustrated in FIG. 12. The connectors 20 are positioned along the vertebral rod 60 with the second receptacles 50 aligning with and receiving the anchor posts. The construct 10 is then moved along the anchor posts to the bone anchors. The retaining members 70 maintain the connectors 20 attached to the vertebral rod 60. In one embodiment, the connectors 20 are loosely positioned on the vertebral rod 60 and generally aligned with the anchor posts by the surgeons. Once aligned, the fasteners 40 are tightened to fix the position.

In another embodiment, the retaining members 70 are attached to the elongated member 60 prior to the connector 20. The first receptacle 26 of the connector 20 is aligned with the end 61 of the elongated member 60. Prior to attachment, the retaining member 70 attached to the end 61 is larger than the first receptacle 26. The first end 61 with the retaining member 70 is aligned with the first receptacle 26 and the connector 20 is moved over the retaining member 70. This movement causes the retaining member 70 to deform to a smaller size to fit within the first receptacle 26. The connector 20 is moved further along the elongated member 60 and eventually moves beyond the retaining member 70. The retaining member 70 than returns to its original shape that is larger than the first receptacle 26 to prevent the detachment of the connector 20. The connector 20 is then moved along and positioned at a central section 66 of the elongated member 60.

The shape of the retaining member 70 may facilitate the deformation to allow the connector 20 to move over the retaining member 70. In one embodiment, the chamfer 75 causes the radial section of the retaining member 70 that extends outward beyond the central section 66 to bend inward against the central section 66. This bending reduces the size and allows for the connector 20 to move past the retaining member 70. The chamfer 75 also forms a funnel that aligns the retaining member 70 within the first receptacle 26 when the connector 20 is being moved onto the elongated member 60. Also, the inner surface 72 is shaped to prevent removal of the retaining member 70. The inner surface 72 may be substantially flat and may be perpendicular to the longitudinal axis A. This forms a barrier that prevents or greatly reduces the likelihood of the retaining member 70 deforming when the connector 20 is moved from the central section 66 towards the end 61.

As illustrated in FIGS. 1, 2, and 4, the connectors 20 may be positioned adjacent to the retaining members 70 with no intervening elements. Therefore, the retaining members 70 alone function to maintain the attachment of the connectors 20 on the elongated member 60.

Figure 13:
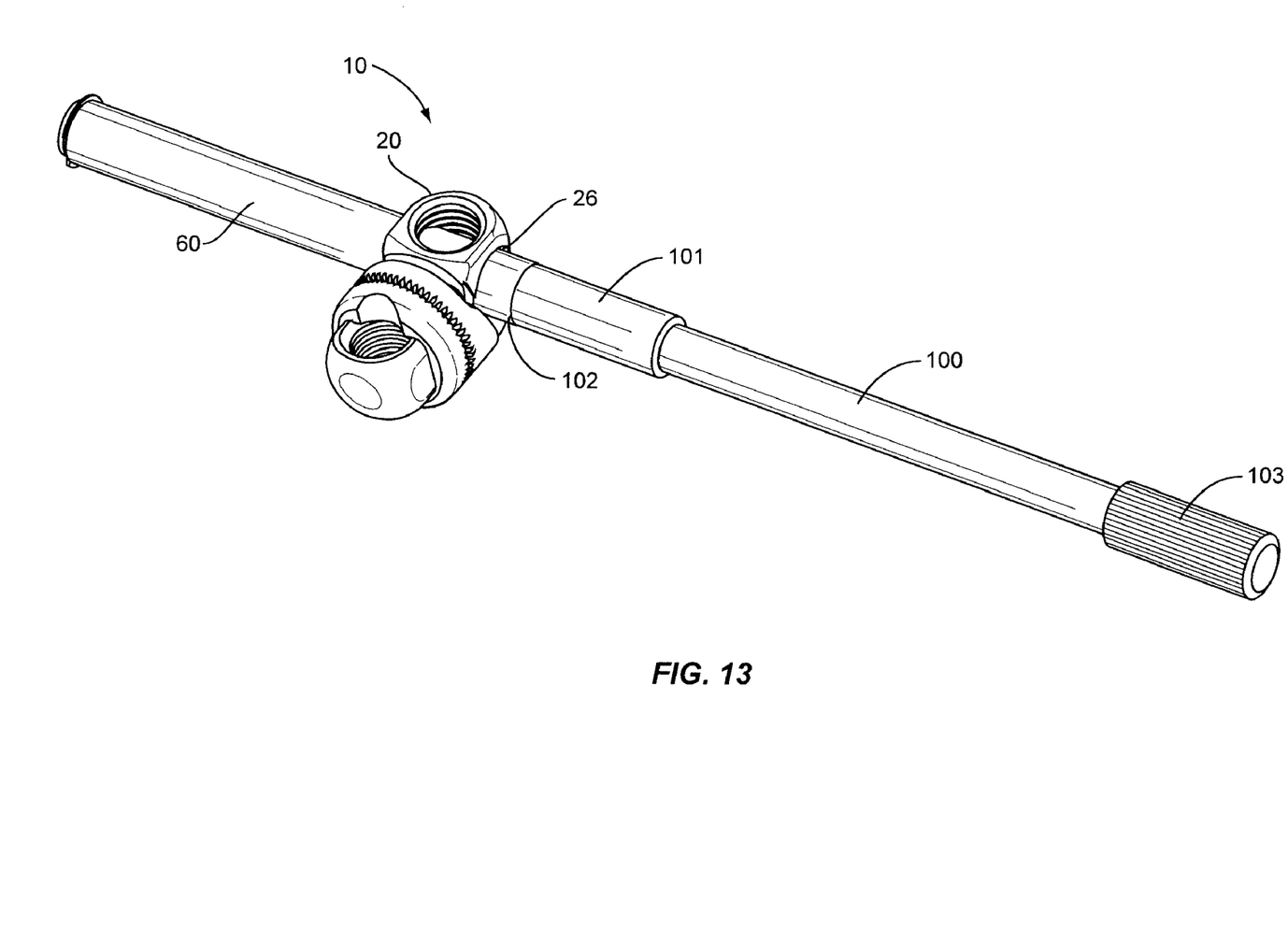
FIG. 13 is a perspective view of a removal instrument attached to a pre-assembled construct according to one embodiment.

FIG. 13 includes a removal instrument 100 for removing the connector 20 from the elongated member 60. The removal instrument includes a shaft with a handle 103 at a proximal end and a receiver 101 with a cavity 102 at a distal end. The cavity 102 is slightly larger than the central section 66. The receiver 101 is also sized smaller than the first receptacle 26. In use, the receiver 101 contacts the retaining member 70 (not illustrated in FIG. 13) and deforms the retaining member 70 similar to the insertion of the connector 20 described above. The deformed retaining member 70 remains within the cavity 102. The receiver 101 may be further moved onto the elongated member 60 and extend over a portion of the enlarged central section 66. The instrument 100 is positioned as illustrated in FIG. 13 and the connector 20 may than be moved along the central section 66. Because the receiver 101 is smaller than the first receptacle 26, the connector 20 is also moved over and onto the receiver 101. The receiver 101 with the connector 20 is then removed from the elongated member 60. Once removed, the connector 20 can be slid off the distal end of the receiver 101.

The constructs 10 may be implanted within a living patient for the treatment of various spinal disorders. The constructs 10 may also be implanted in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A pre-assembled construct that attaches to a structural member in a patient, the pre-assembled construct comprising:
    an elongated member with opposing first and second ends;
    a connector comprising:
        a body;
        a first receptacle that extends through the body and receives the elongated member with the first end positioned on a first side of the connector and the second end positioned on a second side of the connector, the first receptacle being larger than the elongated member for the connector to be movable along the elongated member;
        a threaded aperture that extends from an exterior of the body into the first receptacle;
        a fastener threaded into the threaded aperture and including a thread that extends along first and second longitudinal sections and a thread interrupt positioned between the sections to resist the first section from moving into the threaded aperture, the interrupt and the first section positioned in the first receptacle for a distal end of the fastener to contact against the elongated member;
        a second receptacle spaced away from the first receptacle to receive the structural member in the patient; and
    retaining members permanently attached to each of the first and second ends of the elongated member, each of the retaining members including a central opening with an inner radial surface that contacts the elongated member and an outer radial surface that extends outward beyond the elongated member, each of the retaining members being larger than the first receptacle to prevent the connector from detaching from the elongated member.

2. The pre-assembled construct of claim 1, wherein at least one of the retaining members is constructed from Nitinol and is deformable from a first size that is greater than the first receptacle to prevent the connector from detaching from the elongated member and a deformed second size that is smaller than the first receptacle to move the connector over the retaining member and onto the elongated member.

3. The pre-assembled construct of claim 1, wherein at least one of the retaining members includes a chamfer and includes a greater thickness at the inner radial surface and a smaller thickness at the outer radial surface.

4. The pre-assembled construct of claim 1, wherein at least one of the retaining members includes a gap that leads into the central opening.

5. The pre-assembled construct of claim 1, further comprising threads at the first and second ends of the elongated member that extend inward a limited distance towards a central section of the elongated member and each of the retaining members includes threads on the inner radial surface.

6. The pre-assembled construct of claim 1, wherein each of the retaining members includes an inner axial wall that faces towards a central section of the elongated member that is perpendicular to a longitudinal axis of the elongated member.

7. A pre-assembled construct that attaches to a structural member in a patient, the pre-assembled construct comprising:
- a rod with a non-threaded central section, a first end, and a threaded section that extends inward from a second end towards the central section;
- a connector comprising:
  - a body;
  - a first receptacle that extends through the body and receives the rod with the first end positioned on a first side of the connector and the second end positioned on a second side of the connector;
  - a threaded aperture that extends into the first receptacle;
  - a fastener threaded into the threaded aperture and including a thread with a crest and a valley, the thread further including an interrupt positioned between opposing ends of the thread;
  - a second receptacle spaced away from the first receptacle to receive the structural member in the patient; and
- a first retaining member attached to the first end of the rod and being larger than the first receptacle to prevent the connector from detaching from the first end of the rod; and
- a second retaining member attached to the second end of the rod and including a threaded central opening that mates with the threaded second end of the rod, the second retaining member including an outer radial surface with a larger size than the central section, the second retaining member being larger than the first receptacle to prevent the connector from detaching from the second end of the rod.

8. The pre-assembled construct of claim 7, wherein the second retaining member further includes a plurality of cavities that extend into an outer axial surface between the outer radial surface and an inner radial surface.

9. The pre-assembled construct of claim 7, wherein the second retaining member includes an inner axial surface that is substantially flat and aligned perpendicular to a longitudinal axis of the rod.

* * * * *